United States Patent
Hangai et al.

(10) Patent No.: US 8,641,701 B2
(45) Date of Patent: Feb. 4, 2014

(54) PROBE TYPE DEVICE FOR REMOVING LIVING BODY TISSUE

(75) Inventors: Masanori Hangai, Kyoto (JP); Nagahisa Yoshimura, Kyoto (JP); Masaaki Nakahara, Miyazaki (JP); Kazunori Miyata, Miyazaki (JP); Tetsuya Eguchi, Tokyo (JP); Yasuhiro Osakabe, Tokyo (JP)

(73) Assignees: Kyoto University, Kyoto (JP); Hoya Corporation, Tokyo (JP)

( * ) Notice: Subject to any disclaimer, the term of this patent is extended or adjusted under 35 U.S.C. 154(b) by 0 days.

(21) Appl. No.: 12/449,988

(22) PCT Filed: Mar. 6, 2008

(86) PCT No.: PCT/JP2008/054025
§ 371 (c)(1),
(2), (4) Date: Oct. 20, 2009

(87) PCT Pub. No.: WO2008/108425
PCT Pub. Date: Sep. 12, 2008

(65) Prior Publication Data
US 2010/0106054 A1    Apr. 29, 2010

(30) Foreign Application Priority Data
Mar. 6, 2007   (JP) ................................. 2007-055868

(51) Int. Cl.
*A61B 18/18*    (2006.01)

(52) U.S. Cl.
USPC .................................... 606/2; 606/4; 606/167

(58) Field of Classification Search
USPC .......... 600/562–568; 606/167, 170, 171, 1, 2, 606/427, 32, 34, 39, 40; 607/1, 96
See application file for complete search history.

(56) References Cited

U.S. PATENT DOCUMENTS

| 4,246,902 A | * | 1/1981 | Martinez .......................... 604/22 |
| 4,694,828 A | | 9/1987 | Eichenbaum |
| 4,844,088 A | * | 7/1989 | Kambin ......................... 600/566 |
| 4,976,710 A | * | 12/1990 | Mackin ........................... 606/15 |
| 5,106,364 A | | 4/1992 | Hayafuji et al. |

(Continued)

FOREIGN PATENT DOCUMENTS

| JP | A-03-039155 | 2/1991 |
| JP | B2-2574793 | 1/1997 |

(Continued)

*Primary Examiner* — Max Hindenburg
*Assistant Examiner* — Jonathan M Foreman
(74) *Attorney, Agent, or Firm* — Oliff & Berridge, PLC (57) ABSTRACT

There is provided a probe type living body tissue removing device comprising a probe unit having a probe formed in a capillary tube shape and an opening hole portion for internally aspirating a living body tissue, and also having a dissection device arranged within the probe and dissecting the living body tissue aspirated into the probe from the opening hole portion of the probe; wherein an aspiration force supplying device for supplying aspiration force to the probe unit, and a dissection driving source supplying device for supplying power or energy for fulfilling a function of the dissection device to the probe unit are connected to the probe unit; and the probe type living body tissue removing device dissects, and aspirates and removes the living body tissue by the dissecting means while the probe is inserted into the living body tissue and the living body tissue is aspirated through the opening hole portion; and a plurality of the opening hole portions of the probe are arranged.

9 Claims, 5 Drawing Sheets

(56) References Cited

U.S. PATENT DOCUMENTS

| | | | |
|---|---|---|---|
| 5,275,607 A | * | 1/1994 | Lo et al. ............ 606/169 |
| 5,409,013 A | * | 4/1995 | Clement ............ 600/566 |
| 5,423,798 A | * | 6/1995 | Crow ............ 606/4 |
| 5,474,532 A | | 12/1995 | Steppe |
| 5,843,111 A | | 12/1998 | Vijfvinkel |
| 5,964,716 A | * | 10/1999 | Gregoire et al. ............ 600/564 |
| 6,027,493 A | | 2/2000 | Donitzky et al. |
| 6,464,694 B1 | | 10/2002 | Massengill |

FOREIGN PATENT DOCUMENTS

| | | |
|---|---|---|
| JP | A-11-137594 | 5/1999 |
| JP | A-11-318968 | 11/1999 |
| JP | A-2002-177317 | 6/2002 |
| JP | A-2002-537017 | 11/2002 |
| WO | WO 00/48525 | 8/2000 |

\* cited by examiner

PROBE TYPE DEVICE FOR REMOVING LIVING BODY TISSUE

TECHNICAL FIELD

The present invention relates to a probe type device for removing a living body tissue, which aspirates and removes a gel-like living body tissue such as an eyeball tissue, etc. while the gel-like living body tissue is dissected, and, for example, relates to an effective structure using a vitreous surgery, etc. for example, in, an ophthalmic field.

BACKGROUND ART

In a recent surgery of the ophthalmic field, for example, in a cataract surgery, a surgical manipulative procedure of micro-incision is developed for a reduction of post-operative astigmatism after the surgery, early wound healing, a reduction of endophthalmitis and a reduction of a surgical invasion. Further, in a vitreoretinal surgery, a new surgical technique such as a vitreous surgery for a macular hole, an internal limiting membrane peeling, a submacular surgery, a macular translocation, an optic neurotomy, etc. is also developed. Similarly, a surgical technique using small incision is proposed for the reduction of post-operative astigmatism, the early wound healing, the reduction of endophthalmitis and the reduction of a surgical invasion.

The living body tissue removing device of the probe type for aspirating and removing the gel-like tissue of such as a vitreous body, while being inserted into the living body tissue of such as an eyeball and cutting the gel-like tissue into small pieces, is provided to enable such a surgical technique. This probe type living body tissue removing device has a capillary tubular probe inserted into the gel-like living body tissue of the eyeball tissue, etc. The living body tissue of the vitreous body, etc. is removed by cutting the living body tissue into small pieces and aspirating and removing the small pieces while the living body tissue is aspirated from an opening hole portion arranged on a side face of this probe.

In the gel-like living body tissue of the vitreous body, etc., living body molecules are chained as a fiber. Therefore, to remove this living body tissue, at the same time as the aspiration for partially pulling the tissue from the opening hole portion into the probe, it is necessary to cut this pulled-in tissue portion into small pieces within the probe. As a system of this dissection, there are a system (e.g., patent document 1) using a cutter edge of a mechanical driving type and a system (e.g., patent document 2) using a laser beam. Further, there is also a system using both these systems to raise removal efficiency (e.g., patent document 3).

A portion including the above capillary tubular probe or a hand holder portion for holding this probe is not determined in name definition, and is also called a contact tip or a hand piece, etc.

Patent document 1: Japanese Laid-Open Patent No. 2002-177317
Patent document 2: Japanese Laid-Open Patent No. 11-318968
Patent document 3: Japanese Laid-Open Patent No. 11-137594

DISCLOSURE OF THE INVENTION

Problems to be Solved by the Invention

The above prior art has the following problems. First, in the structure using the cutter edge of the mechanical driving system as the dissection system of the living body tissue partially pulled-into the probe, it is difficult to reduce the diameter of the probe since a movable mechanism is assembled into the probe. Further, cost is increased and maintenance burden is increased by making the structure complicated, and cutting quality is reduced by deteriorating the cutter edge.

On the other hand, the structure using the laser beam as the dissection system has the problem that removal efficiency is not necessarily high. Therefore, for example, in the structure described in patent document 2, an emitting face of the laser beam is set to a flat shape, and this flat emitting face is formed along a probe inner wall face of an opening hole portion upper portion. However, this structure prevents the reduction of the diameter of the probe.

With respect to the removal efficiency, it cannot be said to be sufficient even in the system using the cutter edge, and its improvement is desired. Therefore, as in patent document 3, the system using both the above systems is also proposed. However, in this case, the construction of both the systems is assembled into the probe. Therefore, it is further difficult to reduce the diameter of the probe. Therefore, the problem of the mechanical driving system using the cutter edge is enlarged.

The reduction in the diameter of the probe is a very important subject in e.g., the above-mentioned surgical technique of the micro-incision. However, each of the above conventional probe type living body tissue removing devices has the problem that it is difficult to reduce the diameter of this probe.

If the diameter of the probe can be reduced, an invasion property upon the living body is reduced. On the other side, the rigidity of the probe is also reduced by reducing the diameter of the probe. In accordance with a using part, there are also reductions in surgical efficiency and effect, due to badness of manipulation which this reduction in rigidity causes. Further, a reduction of the removal efficiency due to the diameter reduction itself is also caused. In contrast to this, there is a method for increasing the living body tissue aspirated by restraining a cut rate as an opening-closing cycle and improving the removal efficiency in a mechanical type cutter opened and closed by an aspiration hole of the probe and a cutter edge. However, for example, in the case of the vitreoretinal surgery of the ophthalmic surgery, when the aspirated vitreous body is increased, there is a high possibility that traction of retina is caused by its aspiration force, to thereby cause the likelihood of giving damage to the retina. Therefore, a problem is caused in safety. Therefore, a method in which the aspiration force is restrained by raising the cut rate, etc. and an influence on a portion except for the living body tissue to be removed is restrained, etc. is used. However, it is also difficult to assemble and control a mechanical structure for raising the cut rate.

The present invention is made to solve the above problems, and its object is to consistently attain the reduction in the diameter of the probe and the improvement of the removal efficiency in the probe type living body tissue removing device, and be also able to improve low cost property and maintenance property due to simplification of the structure.

Means for Solving the Problems

The solving means provided by the present invention is as follows.

(1) A probe type living body tissue removing device comprising a probe unit having a probe formed in a capillary tube shape and an opening hole portion for internally aspirating a living body tissue, and also having a dissection device arranged within the probe and dissecting the living body tissue aspirated into the probe from the opening hole portion of the probe;

wherein an aspiration force supplying device for supplying aspiration force for aspirating and removing the living body tissue through the probe unit to the probe unit, and a dissection driving source supplying device for supplying power or energy for fulfilling a function of the dissection device to the probe unit are connected to the probe unit; and the probe type living body tissue removing device dissects, and aspirates and removes the living body tissue by the dissecting means while the probe is inserted into the living body tissue and the living body tissue is aspirated through the opening hole portion; and a plurality of the opening hole portions of the probe are arranged.

(2) The probe type living body tissue removing device according to (1), wherein at least one of the number of opening hole portions of the probe, the shape of the hole, the size of the hole and the position of the hole is variably constructed.

(3) The probe type living body tissue removing device according to (2), wherein the probe type living body tissue removing device has an opening hole adjusting tube fitted so as to be moved and adjusted within the probe such that an outer circumferential face of the opening hole adjusting tube comes in contact with an inner circumferential face of the capillary tubular probe; and at least one of the number of opening hole portions of the probe, the shape of the hole and the size of the hole is changed by adjusting a blocking degree of the opening hole portion of the probe due to this opening hole adjusting tube by moving and adjusting this opening hole adjusting tube.

(4) The probe type living body tissue removing device according to (3), wherein an opening hole for an adjustment is arranged in the opening hole adjusting tube, and at least one of the number of opening hole portions of the probe, the shape of the hole, the size of the hole and the position of the hole is changed by adjusting an overlapping degree of the opening hole for an adjustment and the opening hole portion of the probe by moving and adjusting the opening hole adjusting tube.

(5) The probe type living body tissue removing device according to (1), wherein the dissecting means is a dissection edge arranged so as to be reciprocated in a longitudinal direction within the probe such that an outer circumferential face of the dissection edge comes in contact with an inner circumferential face of the capillary tubular probe; and the living body tissue is dissected by the dissection edge for dissecting the living body tissue by reciprocating this dissection edge.

(6) The probe type living body tissue removing device according to (1), wherein the dissecting means has a light guide body for emitting a laser beam toward an inside space portion of the opening hole portion of the probe, and the living body tissue is dissected by the laser beam emitted from this light guide body.

(7) The probe type living body tissue removing device according to (6), wherein the light guide body is an optical fiber arranged within the probe, and an aspiration-exhaust path of the dissected living body tissue is formed between this optical fiber and an inner wall of the probe.

(8) The probe type living body tissue removing device according to (1), wherein the outer diameter of the probe is 20G or more (about 0.9 mm or less).

(9) The probe type living body tissue removing device according to (6), wherein one of Er:YAG laser, Ho:YAG laser and Nd:YAG laser is used as the laser beam for dissecting the living body tissue.

(10) The probe type living body tissue removing device according to (6), wherein the light guide body is a quartz or sapphire fiber.

(11) A probe unit having a probe formed in a capillary tube shape and an opening hole portion for internally aspirating a living body tissue, and also having a dissection device arranged within the probe and dissecting the living body tissue aspirated into the probe from the opening hole portion of the probe;

wherein an aspiration force supplying device for supplying aspiration force for aspirating and removing the living body tissue through the probe unit to the probe unit, and a dissection driving source supplying device for supplying power or energy for fulfilling a function of the dissection device to the probe unit are connected to the probe unit; and the probe unit is used in a probe type living body tissue removing device which dissects, and aspirates and removes the living body tissue by the dissecting means while the probe is inserted into the living body tissue and the living body tissue is aspirated through the opening hole portion; and a plurality of the opening hole portions of the probe are arranged.

Effect of the Invention

In the probe type living body tissue removing device, it is possible to consistently attain the reduction in the diameter of the probe and the improvement of the removal efficiency, and improve the low cost property and the maintenance property due to the simplification of the structure. A function effect except for the above will become apparent in the description of this specification and the accompany drawings.

BEST MODE FOR CARRYING OUT THE INVENTION

Figure 1:
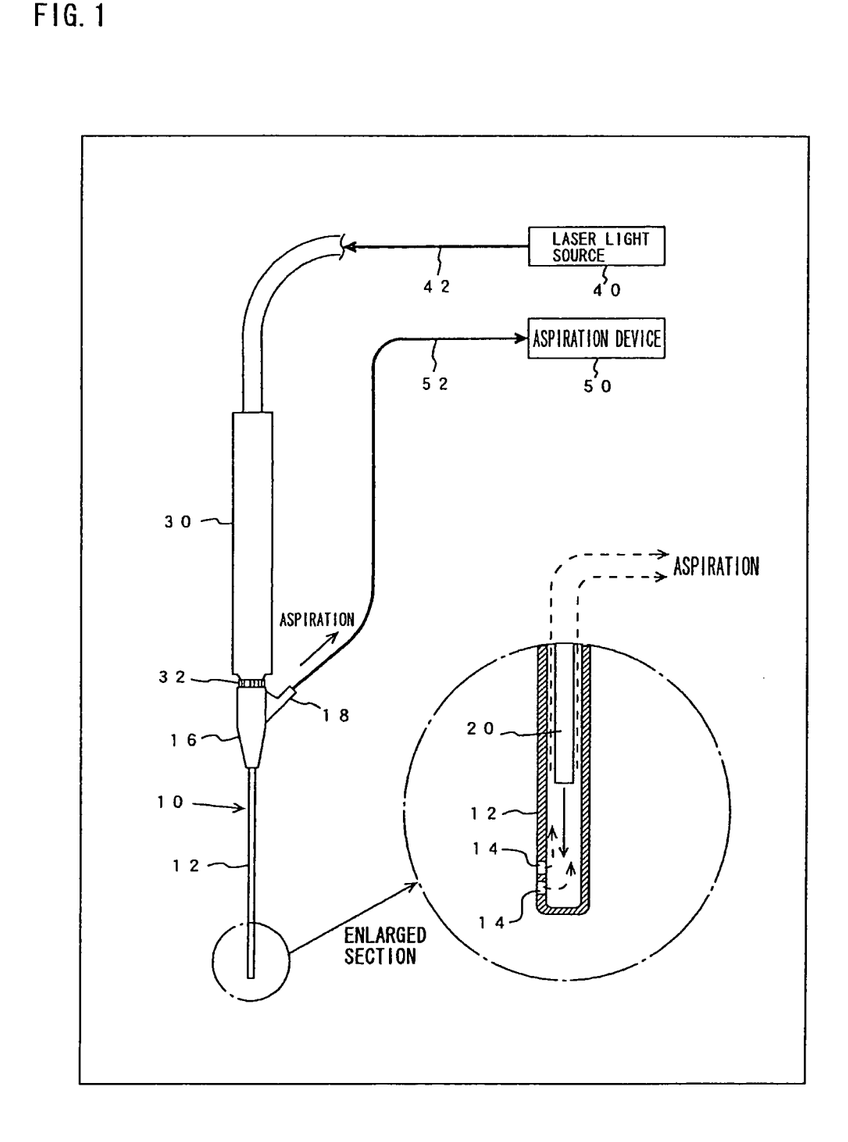
[FIG. 1] A partial enlarged side schematic view showing one embodiment mode of a probe type living body tissue removing device to which the technique of the present invention is applied.

FIG. 1 shows one embodiment mode of a probe type living body tissue removing device in accordance with the present invention. The probe type living body tissue removing device shown in this figure is constructed by a probe unit section 10, a holder portion 30, a laser light source 40, a aspirating device 50, etc. The above aspirating device 50 corresponds to an aspiration force supplying device for supplying aspiration force for aspirating and removing a living body tissue, to the probe unit through the above probe unit section 10. The above laser light source 40 corresponds to a dissection driving source supplying device for supplying energy for fulfilling the function of a dissection device using a laser beam described later and arranged in the above probe unit to the above probe unit. The device of this kind is also called a contact tip or a hand piece, etc., but the device in accordance with the present invention can be also used in the same object as these.

The probe unit section 10 is constructed by a probe 12 and an optical fiber 20 arranged within the probe 12, and is attached to a fixture 16. The probe 12 is formed by using a capillary tube of a corrosion-resisting metal such as SUS, etc. A base end portion of this probe 12 is attached to the fixture 16, and a plurality of opening hole portions 14 are arranged in a side face portion close to a tip portion of the probe 12.

The optical fiber 20 is inserted into the probe 12 in a coaxial shape. This optical fiber 20 constitutes a light guide body for guiding and emitting the laser beam. A tip face forming a laser beam emitting face of this optical fiber 20 is directed to an inside space portion of the above opening hole portion 14. Namely, the laser beam is emitted in a tip direction of the probe 12.

An aspiration port 18 is arranged in this probe unit section 10, and this probe unit section 10 is detachably connected to the holder portion (also called a hand piece) 30 through a connecting tool 32. Thus, the probe unit section 10 can be used as a probe unit which is an exchanging part able to be attached and detached, and the probe 12 can be simply divisionally used in accordance with new product exchange and uses of the probe 12. In this case, if the probe unit has only a member of a minimum limit (a jig or a boss member, etc.) for detachably mounting the probe 12 to the removing device, it is possible to minimize and economically use an exchanging portion.

The aspiration port 18 is communicated and connected to the aspirating device 50 through a flexible aspiration tube 52. Further, a flexible light guide cable 42 for transmitting a pulse-shaped laser beam outputted from the laser light source 40 is pulled into the holder portion 30.

An optical coupler (not shown in the drawings) for inputting emitted light of the light guide cable 42 to the optical fiber 20 within the probe 12 in a state connecting both the probe unit section 10 and the holder portion 30 through the connecting tool 32, is formed between the probe unit section 10 and the holder portion 30.

The optical fiber 20 as a light guide body is inserted into the probe 12 in a coaxial shape, but a aspirating-exhausting path of a living body tissue cut into small pieces is formed between this optical fiber 20 and the probe 12. The probe 12 is formed to have a small diameter of 20 G or more (about 0.9 mm or less) in outer diameter, and the plurality of independent opening hole portions 14 are mutually adjacently arranged on a side face close to a tip portion of the probe 12.

It is preferable that the probe 12 has a small diameter of 25 G (about 0.5 mm) from the viewpoint of a low invasion property onto the living body. However, rigidity is deteriorated by reducing the diameter, thus deteriorating the efficiency of manipulation and an aspiration effect. Accordingly, 20 G (about 0.9 mm) is preferable if the efficiency and the rigidity are preferential. Further, according to a disease case, an intermediate diameter 23 G (about 0.6 mm) is suitably selected in consideration of a balance of the low invasion property and the efficiency-effect.

The laser light source 40 is not particularly limited, but it is particularly desirable that the laser light source 40 oscillates the laser beam of a wavelength easily absorbed to water. Specifically, Er:YAG laser, Ho:YAG laser, Nd:YAG laser are suitable. In particular, Er:YAG laser oscillates the laser beam near a wavelength of 2.94 μm having a singularly high absorption coefficient with respect to water. Accordingly, in the living body tissue containing a lot of water, Er:YAG laser is suitable since a thermal influence on a peripheral tissue is little. Further, there is also opaque formation of the tissue due to heat in an eyeball tissue particularly having many transparent portions, and Er:YAG laser is most suitable in utilization to the present invention.

An optical fiber having good transmission efficiency of the laser is generally selected as the optical fiber 20, and a quartz or sapphire fiber is preferable. When Er:YAG laser is used, a sapphire fiber of good transmission efficiency is particularly preferable.

In the probe type living body tissue removing device constructed as mentioned above, while the aspiration within the probe 12 using the aspirating device 50 is performed in a state in which the probe 12 is inserted into a gel-like living body tissue of an eyeball tissue, etc., the laser beam is emitted in a pulse shape toward an inside space portion of the opening hole portion 14.

Thus, one portion of the living body tissue is pulled into the probe 12 from the opening hole portion 14. This partially pulled-in tissue is dissected by the laser beam pulse. The dissected tissue pieces are aspirated and removed in the aspirating device 50 from the interior of the probe 12 through the flexible aspiration tube 52. When the laser beam is irradiated to the living body tissue and this living body tissue is soft as in a vitreous body fiber, the intermolecular bond of a fiber layer of this living body tissue is separated and a state similar to liquefaction is attained and the tissue pieces are aspirated and removed.

Thus, the living body tissue can be removed, but this removing mechanism is also basically the same in the conventional device. However, it should be here noticed that the number of opening hole portions 14 for partially pulling the living body tissue into the probe 12 is conventionally one, but the plurality of opening hole portions 14 are divisionally arranged in the present invention.

It is conventionally necessary to efficiently pull the gel-like living body tissue into the probe and dissect this living body tissue so as to efficiently remove the gel-like living body tissue. Therefore, it has been considered that it is effective to increase the opening diameter of the opening hole portion arranged in the probe as much as possible.

However, in accordance with the knowledge obtained by the present inventors, it has become clear that the removal efficiency is not necessarily improved even when the opening diameter of this opening hole portion is increased. Further, although it is opposed to the conventional idea, the present inventors have known that, even when the opening diameter of the opening hole portion 14 is reduced, the arrangement of the plurality of these small opening hole portions 14 greatly contributes to an improvement of the removal efficiency.

This is unexpected knowledge not anticipated in the prior art at all. However, the probe type living body tissue removing device of the above embodiment mode constructed on the basis of this novel knowledge can reduce the diameter and cost of the probe 12 by a simple structure using no cutter edge of the mechanical driving type. The removal efficiency can be greatly improved together with this.

The reason of improving the removal efficiency by divisionally arranging the plurality of opening hole portions 14 is not certain, but the following matters are considered. Namely, the living body tissue is pulled into the probe 12 in a state respectively divided into small pieces in the plurality of opening hole portions 14. Therefore, the dissection using the laser beam is individually performed with respect to this divided tissue portion. At this time, it is considered that the dissection using the laser beam is efficiently performed in the individual case with respect to the plurality of tissue portions divided into small pieces in comparison with a collective case with respect to one large tissue portion. Further, in the latter case, it is considered that the size of the tissue piece cut into small pieces is reduced so that its aspiration removal becomes smooth. It is considered that the great improvement of the removal efficiency is attained in cooperation with these.

In any case, the plurality of opening hole portions 14 for aspiration arranged in the probe 12 are divisionally arranged so that the removal efficiency can be greatly improved by a construction very suitable for the reduction in the diameter of the probe 12 without causing the structure to be complicated.

Figure 2:
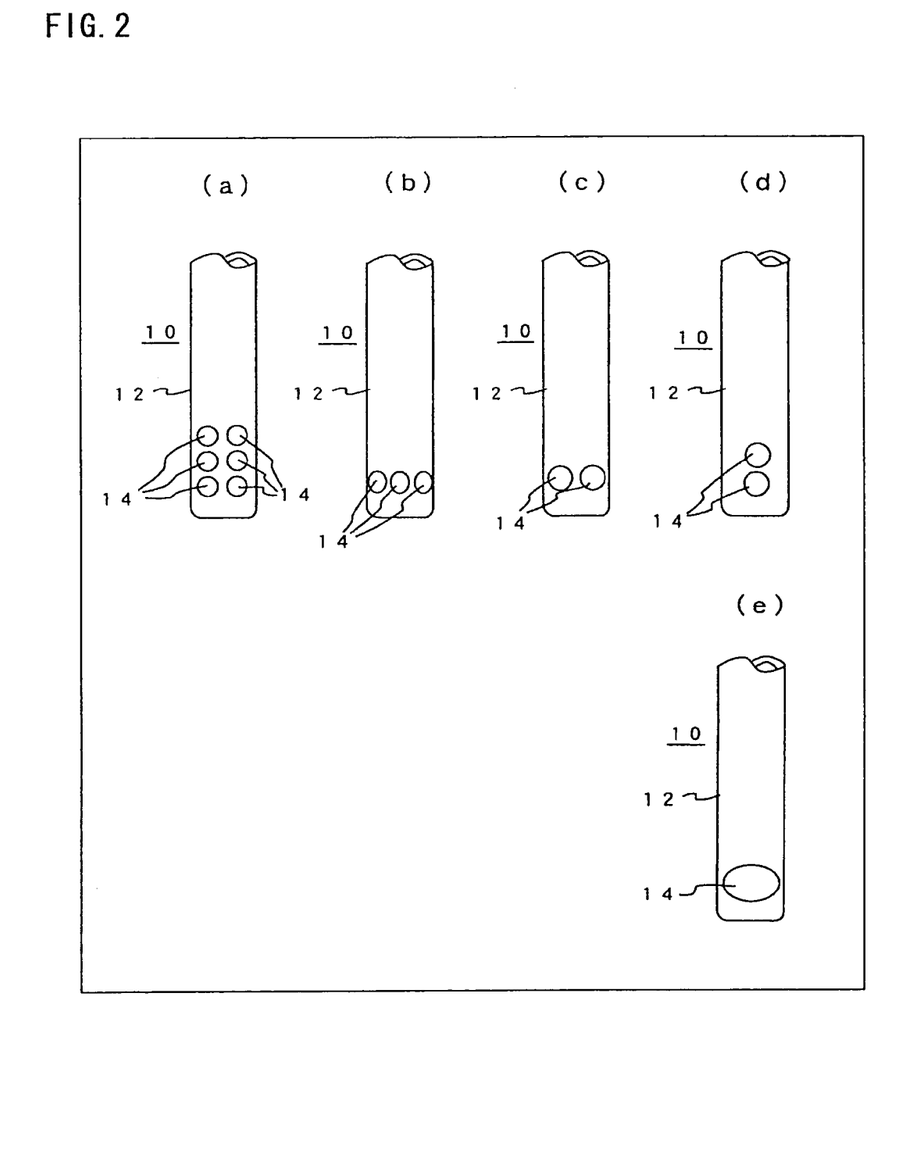
[FIG. 2] A view showing various embodiment modes of a probe constituting a main portion of the present invention.

FIG. 2 shows a constructional example of the above opening hole portion 14. In the device in accordance with the present invention, as shown in FIGS. 2(a) to 2(d), the opening hole portion 14 is divisionally arranged in at least two or more. In this case, as shown in FIG. 2(e), when the number of opening hole portions 14 is only one, it has become clear that the opening diameter can be increased, but the removal efficiency greatly depends on the divisional number of the opening hole portion 14 in comparison with its opening diameter.

Figure 3:
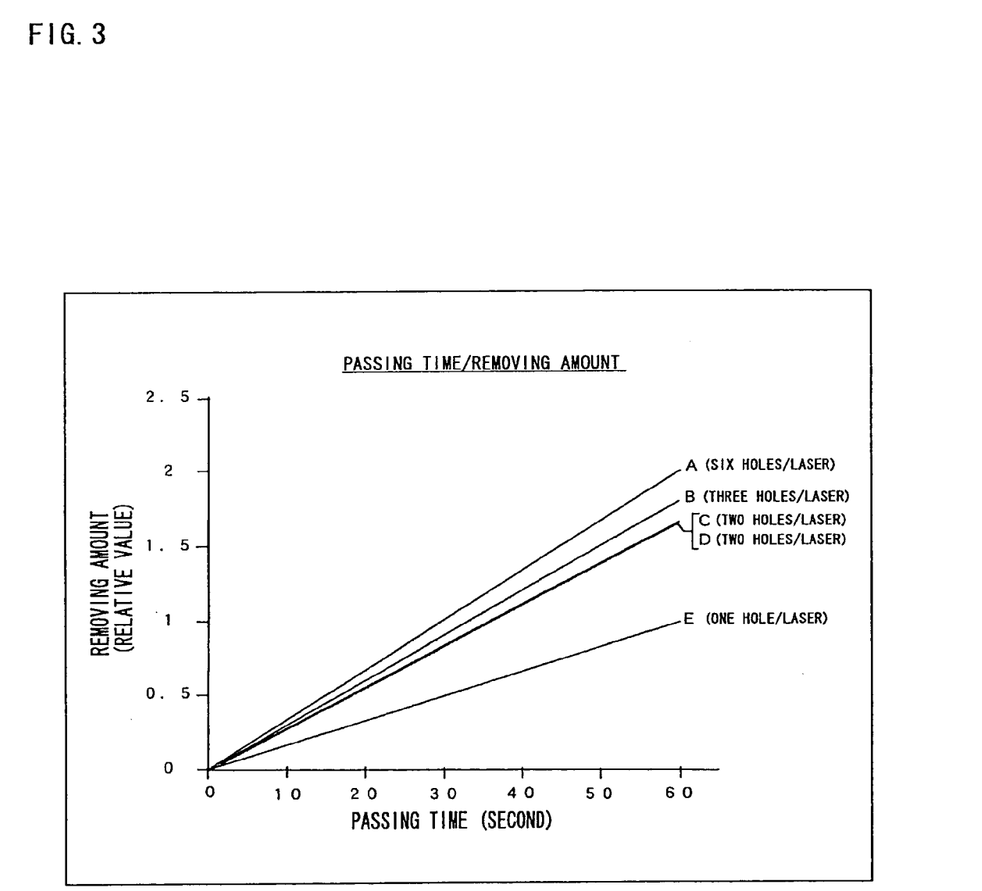
[FIG. 3] A graph showing the relation of an arrangement number of an opening hole portion of the probe and removal characteristics.

FIG. 3 shows the relation of an arrangement number of the opening hole portion 14 of the probe 12 and removal characteristics by a graph. In this figure, graph lines A to E respectively show the relation of removal time (axis of abscissa) and a removing amount (axis of ordinate) when the eyeball tissue (vitreous body) of a pig is removed by the probe 12 shown in FIGS. 2(a) to 2(e). With respect to a pig eyeball vitreous body removal weight in the evaluation of vitreous body removal efficiency, the weight after the removal is measured from the weight of the entire pig eyeball before the removal, and a reducing amount is set to the vitreous body removal weight, and comparison is performed with the passage of time. A capillary tube of 0.9 mm in outer diameter (0.58 mm in inner diameter) is used in each probe, and Er:YAG laser is used in the laser light source for the dissection. The laser beam is emitted through the optical fiber of 0.44 mm in outer diameter in a pulse of 80 mJ in laser output and 50 msec in period.

Graph lines A to E respectively show the removal characteristics of the probe 12 shown in FIGS. 2(a) to 2(e). As clearly seen from this comparison of graph lines A to E, in the probe 12 of each of FIGS. 2(a) to 2(d) having the plurality of opening hole portions 14, the removal efficiency is greatly improved in comparison with the probe 12 of FIG. 2(e) having the single opening hole portion 14. In particular, in the probe 12 of FIG. 2(a) having six opening hole portions 14, a total opening area of these six opening hole portions 14 is almost the same as the opening area of the single opening hole portion 14 of FIG. 2(e), but a very big difference appears in the removal efficiency.

Figure 4:
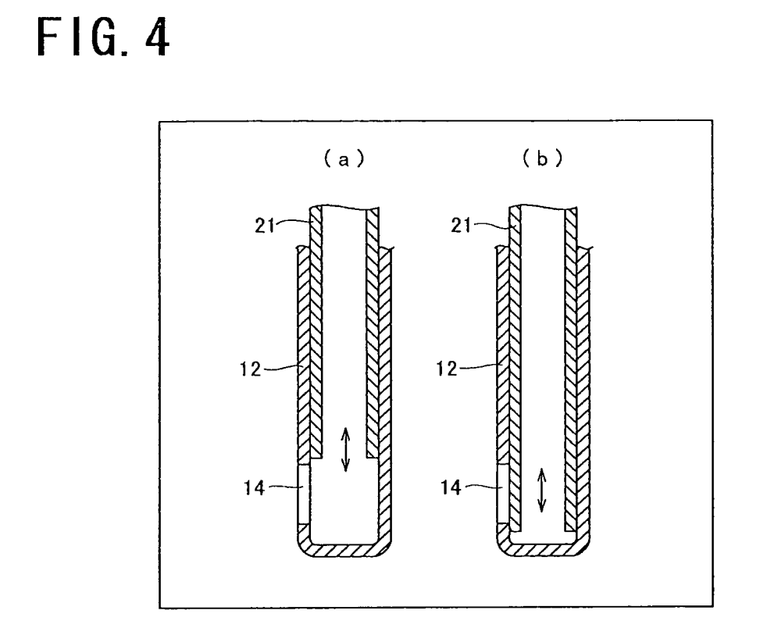

Next, a test of the following combination is made to set up standards of (1) a difference of the removal efficiency due to the material of the optical fiber 20, (2) a difference of the removal efficiency due to the difference of a dissection system, and (3) a difference of the removal efficiency due to the difference between the (conventional) case of one opening hole portion and the (present application) case of six opening hole portions. Namely, first, the test is divisionally made in a case using a quartz fiber and a case using a sapphire fiber as a light guide body. With respect to the laser beam at this time, Er-YAG laser of 2.94 μm in wavelength is used. Further, in this case, the probe unit 10 has two combinational cases and the test is made separately. Namely, the two combinational cases are constructed by a case using a so-called laser vitreous body cutter for dissecting and liquefying the vitreous body by the laser beam shown in the above embodiment mode, and a case using the so-called mechanical type cutter for mechanically dissecting the tissue. Further, the test is made by divisionally setting the conventional case of one opening hole portion and the case of the present application of six opening hole portions. In this case, in the test of the conventional case of one opening hole portion and the case of the mechanical type in the dissection system, a system equal to the aculas 23G system (commercial name of Alcon corporation) manufactured by Alcon corporation is used. The diameter of the probe is set to 23G in each case. With respect to the pig eyeball vitreous body removal weight in the evaluation of the vitreous body removal efficiency, the weight after the removal is measured from the weight of the entire pig eyeball before the removal, and a reducing amount is set to the vitreous body removal weight, and is converted into a value per one second, to thereby perform comparison. FIG. 4 is a partial sectional view of the probe unit using the mechanical type cutter. FIG. 4(a) is a view showing a state in which a cutting edge 21 is located in a position before the dissection. FIG. 4(b) is a view showing a state in which the cutting edge 21 is located in a position after the dissection. As shown in FIG. 4, in the probe unit using the mechanical type cutter, the living body tissue aspirated from the plurality of opening hole portions 14 of the above probe 12 is dissected by reciprocating the dissection edge 21 fitted into the above probe 12 in a longitudinal direction such that an outer circumferential face of the dissection edge 21 comes in contact with an inner circumferential face of this probe 12.

Its result is shown in the following tables.

TABLE 1

Test example of pig eyeball glass body removal weight (mg/sec) by 23G laser probe

| | hole shape (laser: light guide body) | laser oscillation setting (Hz, mJ) | suction (ml/min) | glass body removal weight (mg/sec) |
|---|---|---|---|---|
| test example 1 | one hole (Er-YAG: sapphire) | 20, 80 | 500 | 26.9 ± 2.23 |
| test example 2 | one hole (Er-YAG: quartz) | 20, 80 | 500 | 19.7 ± 2.05 |
| test example 3 | one hole (Er-YAG: sapphire) | 20, 80 | 300 | 17.0 |
| test example 4 | six holes (Er-YAG: sapphire) | 20, 80 | 500 | 24.2 |
| test example 5 | six holes (Er-YAG: sapphire) | 20, 80 | 300 | 19.3 |

TABLE 2

Test example of pig eyeball glass body removal weight (mg/sec) using mechanical type cutter Aculas 23G system manufactured by Alcon corporation

| | | cut rate (c.p.m) | suction (ml/min) | glass body removal weight (mg/sec) |
|---|---|---|---|---|
| test example 6 | Aculas 23G | 1000 | 500 | 25.5 ± 3.83 |
| test example 7 | Aculas 23G | 2500 | 500 | 13.7 ± 1.88 |

In test example 1 (table 1) using the sapphire fiber as a light guide body, it has become clear that the vitreous body removal weight is much and the efficiency is improved under the same condition in comparison with test example 2 (table 2) using the quartz fiber. Further, the aspiration force of test example 6 (table 2) is equal (500 ml/min), and the vitreous body removal weight of the mechanical type cutter (1000 c.p.m) restraining the cut rate is equal to or more. Therefore, a possibility able to realize efficiency equal to that of the mechanical type cutter or more, is suggested. Further, in test example 4 (table 1) of six holes with normal holes as multiple hole types with similar aspiration force, a possibility able to obtain efficiency approximately similar to that of test example 6, is also suggested. Further, when test example 7 of the mechanical type cutter raising the cut rate and test example 3 restraining the aspiration force to reduce damage of a portion except for the removed living body tissue so as to secure safety are compared, the vitreous body removal weight is much and it is effective in efficiency even when the aspiration force is reduced. Further, it is guessed in test example 5 of six holes as the multiple hole type that its effect is particularly notable.

As mentioned above, in the probe type living body tissue removing device in accordance with the present invention, the plurality of opening hole portions 14 are arranged in the probe 12, and the laser beam is emitted to the inside space portion of these plurality of opening hole portions 14. Thus, it is possible to consistently attain the reduction in the diameter of the probe and the improvement of the removal efficiency. Further, low cost property and maintenance property can be also improved by structural simplification.

In this case, the above opening hole portion 14 is preferably arranged on the side face of the probe 12 to raise a dissection effect using the laser beam. Further, if it is the side face of the probe 12, the plurality of opening hole portions 14 can be easily arranged, which is preferable when the dissection effect is further raised. Further, the removal efficiency is raised when the tissue is finely aspirated and is removed by the laser little by little. Thus, it has been found that aspiration efficiency is improved by a hole number when the opening hole area (size) of the aspiration hole is constant. Further, it has been found that the removal efficiency is controlled by changing its hole shape and the hole number, and it is possible to select whether an invasion onto the peripheral tissue should be considered according to the aspirated part and tissue.

Further, the optical fiber 20 is used as the light guide body within the probe 12, and this optical fiber 20 is inserted into the probe 12 in a coaxial shape, and an aspiration-exhaust path of the dissected living body tissue is formed between this optical fiber 20 and the probe 12. The limited inner diameter can be efficiently used by such a construction. Accordingly, the diameter of the probe 12 can be further reduced. For example, the probe, with reduced diameter of 0.9 mm or less can be also comparatively easily realized. When the outer diameter of the probe is reduced to be 0.9 mm or less, a surgical technique using small incision can be performed and the reduction of post-operative astigmatism, early wound healing, the reduction of endophthalmitis and the reduction of a surgical invasion can be performed. Accordingly, the outer diameter of the probe in this case is preferably reduced to be 20G (about 0.9 mm) or less, and the effect of the reduction of the surgery invasion, etc. can be expected in 25G (about 0.5 mm). However, the efficiency of manipulation and the aspiration effect are deteriorated by reducing the diameter. Therefore, if the aspiration effect, the efficiency and the rigidity are preferential, 20G (about 0.9 mm) is preferable. Otherwise, an intermediate diameter 23G (about 0.6 mm) is preferable in view of low invasion property and efficiency and effect. The outer diameter of the probe is suitably selected in accordance with its disease case.

As mentioned above, Er:YAG laser, Ho:YAG laser and Nd:YAG laser are suitable as the laser beam for dissecting the living body tissue. However, Er:YAG laser among these lasers particularly oscillates the laser beam near 2.94 μm in wavelength singularly having a high absorption coefficient for water. Accordingly, Er:YAG laser is suitable in the living body tissue containing a lot of water since a thermal influence on the peripheral tissue is little. In particular, there is also opaque formation of the tissue due to heat in an eyeball tissue having many transparent portions. Accordingly, Er:YAG laser is most suitable in utilization to the present invention. An optical fiber of good transmission efficiency of the laser is generally selected in the optical fiber constituting the light guide body for guiding and emitting the laser beam. However, when this Er:YAG laser beam is used, the light guide body constructed by synthetic quartz (in which the content of a hydroxyl group is reduced to achieve low loss) with small transmission loss in its oscillating wavelength 2.94 μm and comparatively high mechanical strength, or sapphire is preferable. Further, a sapphire fiber is preferable in view of a specific efficiency as a fiber of good transmission efficiency of Er:YAG laser. The removal efficiency is raised by its high efficiency, and the aspiration force can be restrained on the other side. Accordingly, damage of a portion except for the removed living body tissue can be reduced, which is also preferable from the viewpoint of safety.

Figure 5:
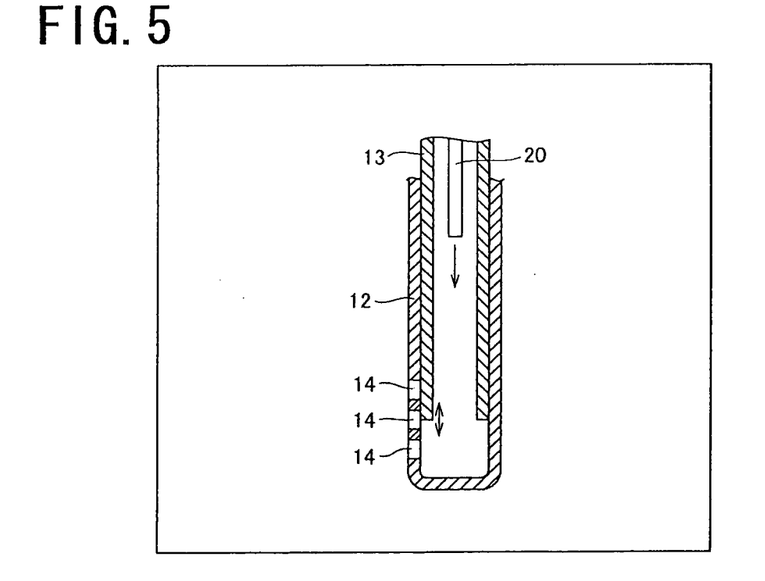
[FIG. 5] A sectional view showing one example of the probe unit able to change at least one of the number of opening hole portions, the shape of the hole and the size of the hole by adjusting a blocking degree of the opening hole portion of a capillary tubular probe.

Further, the above embodiment mode uses an example in which the number of opening hole portions 14 of the probe 12, the shape of the hole, the size of the hole or the position of the hole is fixed. However, at least one of these values may be also changed. FIG. 5 is a sectional view showing one example of a probe unit able to change at least one of the number of opening hole portions, the shape of the hole and the size of the hole by adjusting a blocking degree of the opening hole portion of the capillary tubular probe. As shown in FIG. 5, this probe unit 10 has an opening hole adjusting tube 13 fitted so as to be moved and adjusted within the above probe such that an outer circumferential face of the opening hole adjusting tube 13 comes in contact with an inner circumferential face of this probe 12. The blocking degree of the opening hole portion 14 due to this opening hole adjusting tube 13 is adjusted by moving and adjusting this opening hole adjusting tube 13. For example, as shown by an arrow in FIG. 5, the position of the opening hole adjusting tube 13 is moved and adjusted in the longitudinal direction of the probe 12, or a rotating movement is made with the central axis of the probe 12 as a rotating axis, or a moving adjustment combining these movements is made. Thus, the number of opening hole portions 14 of the above probe 12, the shape of the hole, the size of the hole, etc. can be substantially changed.

Figure 6:
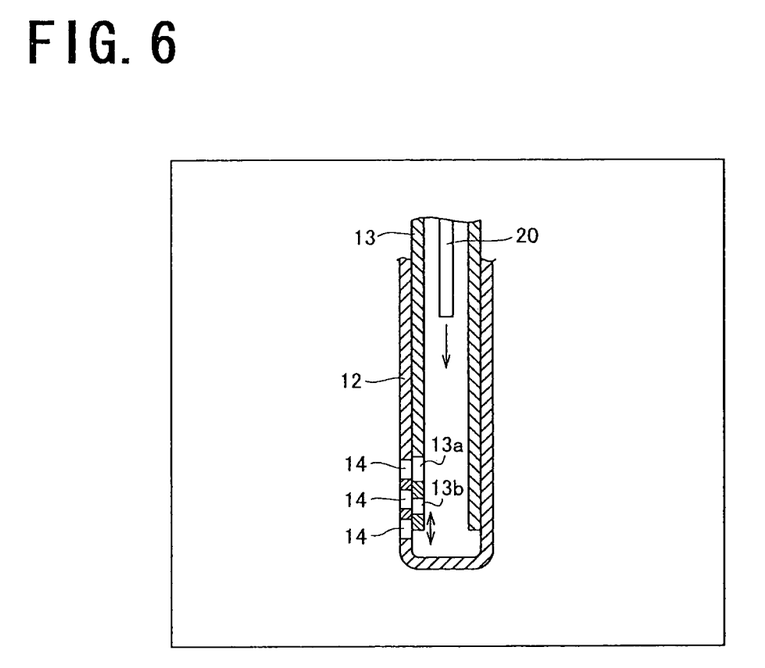
[FIG. 6] A sectional view showing another example of the probe unit able to change at least one of the number of opening hole portions, the shape of the hole, the size of the hole and the position of the hole by adjusting the blocking degree of the opening hole portion of the capillary tubular probe.

FIG. 6 is a sectional view showing another example of the probe unit able to change at least one of the number of opening hole portions, the shape of the hole, the size of the hole and the position of the hole by adjusting the blocking degree of the opening hole portion of the capillary tubular probe. As shown in FIG. 6, in this probe unit 10, an opening hole 13a for an adjustment is further arranged in the opening hole adjusting tube 13 shown in FIG. 5. An overlapping degree of the above opening hole 13a for an adjustment and the opening hole portion 14 of the above probe is adjusted by rotating, moving and adjusting the above opening hole adjusting tube 13 in the vertical direction. Thus, at least one of the number of opening hole portions of the above probe, the shape of the hole, the size of the hole and the position of the hole is changed. Although it is not shown in the drawings, in this case, if a large opening hole portion is arranged in the probe 12 instead of the arrangement of the plurality of opening hole portions 14, and the opening hole 13a for an adjustment of the above opening hole adjusting tube 13 is set to be arranged within this large opening hole portion, and the opening hole adjusting tube 13 is then moved and adjusted, the position of the opening hole 13a for an adjustment can be moved. In the above case, the number of opening hole portions of the probe, the shape of the hole, the size of the hole or the position of the hole, etc. are changed by setting the probe to a double tube structure. However, further, the probe may be set to a triple tube structure, or a mechanism utilizing the principle of a diaphragm mechanism of a camera, etc. may be also used.

As mentioned above, the present invention has been explained on the basis of its typical embodiment, but various modes except for the above modes can be used in the present invention. For example, the opening hole portion 14 can be suitably changed in accordance with a use, etc. For example, the opening hole portion 14 may be also arranged on the tip face of the probe 12. Further, the present invention can be also applied to removal of the gel-like living body tissue or a living body high molecule except for the eyeball tissue. Further, the present invention can be also utilized in the removal of the solidified living body high molecule harder than the gel by performing liquefaction and aspiration and cutting by a laser in contrast to physical cutting in the mechanical type.

Industrial Applicability

In the probe type living body tissue removing device, it is possible to consistently attain the reduction in the diameter of the probe and the improvement of the removal efficiency, and also improve low cost property and maintenance property due to structural simplification.

BRIEF DESCRIPTION OF THE DRAWINGS

[FIG. 4] A partial sectional view of a probe unit using a mechanical type cutter where FIG. 4(a) is a view showing a state in which a cutting edge 21 is located in a position before dissection, and FIG. 4(b) is a view showing a state in which the cutting edge 21 is located in a position after the dissection.

Explanation of Letters or Numerals 10 probe unit section,
12 probe,
13 opening hole adjusting tube,
13a opening hole for an adjustment,
14 opening hole portion,
16 fixture,
18 aspiration port,
20 optical fiber (light guide body),
21 cutting edge,
30 holder portion,
32 connecting tool,
40 laser light source,
42 flexible light guide cable,
50 aspirating device,
52 flexible aspiration tube.

The invention claimed is:

1. A probe type living body tissue removing device comprising:
    a probe unit for performing dissection while aspirating a living body tissue, the probe unit having a base end portion;
    a hand piece for holding the probe unit;
    a connecting tool detachably connecting the probe unit to the hand piece, the connecting tool being located in line between the hand piece and the probe unit;
    an aspiration force supplying device for supplying aspiration force for aspirating and removing the living body tissue to the probe unit; and
    a dissection driving source supplying device for supplying power or energy for dissecting the living body tissue in the probe unit;
    said probe unit comprising:
        a probe formed in a capillary tube shape;
        a plurality of opening hole portions provided in the probe, for aspirating the living body tissue into the probe;
        a dissecting device provided inside of the probe, for dissecting the living body tissue aspired into the probe through the plurality of opening hole portions by the aspiration force supplied from the aspiration force supplying device, by the power or the energy supplied from the dissection driving source supplying device; and
        an aspiration port provided between the connecting tool and the probe, for removing the living body tissue dissected by the dissecting device through an inside of the probe, by introducing the aspiration force supplied from the aspiration force supplying device to the inside of the probe, the living body tissue exits the probe unit via the aspiration port, wherein
    the dissection driving source supplying device is a laser light source for supplying a laser beam to the probe unit for dissecting the living body tissue,
    the dissecting device has a light guide body for emitting the laser beam toward an inside space portion of the opening hole portions of the probe, and is configured to dissect the living body tissue by the laser beam emitted from the light guide body, without using a cutter of a mechanical driving system,
    the laser beam is an Er:YAG laser, and
    the light guide body is a sapphire fiber.

2. The probe type living body tissue removing device according to claim 1, wherein at least one of a number of opening hole portions of the probe, a shape of the hole, a size of the hole and a position of the hole is variably constructed.

3. The probe type living body tissue removing device according to claim 2, wherein
    the probe type living body tissue removing device has an opening hole adjusting tube fitted to be moved and adjusted within the probe such that an outer circumferential face of the opening hole adjusting tube comes in contact with an inner circumferential face of the capillary tubular probe, and
    at least one of the number of opening hole portions of the probe, the shape of the hole and the size of the hole is changed by adjusting a blocking degree of the opening hole portion of the probe due to the opening hole adjusting tube by moving and adjusting the opening hole adjusting tube.

4. The probe type living body tissue removing device according to claim 3, wherein
    an opening hole for an adjustment is arranged in the opening hole adjusting tube, and
    at least one of the number of opening hole portions of the probe, the shape of the hole, the size of the hole and the position of the hole is changed by adjusting an overlapping degree of the opening hole and the opening hole portion of the probe by moving and adjusting the opening hole adjusting tube.

5. The probe type living body tissue removing device according to claim 1, wherein an aspiration-exhaust path of the dissected living body tissue is formed between the sapphire fiber and an inner wall of the probe.

6. The probe type living body tissue removing device according to claim 1, wherein an outer diameter of the probe is 20 G or more (about 0.9 mm or less).

7. A probe unit, which is detachably connected to a hand piece by a connecting tool located in line to the hand piece and the probe unit, said probe unit comprising:
- a probe formed in a capillary tube shape;
- a plurality of opening hole portions provided in the probe, for aspirating a living body tissue into the probe; and
- a dissecting device arranged within the probe for dissecting the living body tissue aspirated into the probe from the opening hole portions of the probe by an aspiration force supplied from an aspiration force supplying device through an aspiration port for aspirating and removing the living body tissue by power or energy supplied from a dissection driving source supplying device, the aspiration port being located between the connecting tool and the probe, the living body tissue exits the probe unit via the aspiration port, wherein the dissection driving source supplying device is a laser light source for supplying a laser beam to the probe for dissecting the living body tissue, the dissecting device has a light guide body for emitting the laser beam toward an inside space portion of the opening hole portions of the probe, and is configured to dissect the living body tissue by the laser beam emitted from the light guide body, without using a cutter of a mechanical driving system, the laser beam is an Er:YAG laser, and the light guide body is a sapphire fiber.

8. The probe type living body tissue removing device according to claim 1, wherein the living body tissue is a gel-like living body.

9. The probe type living body tissue removing device according to claim 8, wherein the gel-like living body is a vitreous.

* * * * *